United States Patent
Baum et al.

(10) Patent No.: US 7,094,284 B2
(45) Date of Patent: Aug. 22, 2006

(54) SOURCE REAGENT COMPOSITIONS FOR CVD FORMATION OF HIGH DIELECTRIC CONSTANT AND FERROELECTRIC METAL OXIDE THIN FILMS AND METHOD OF USING SAME

(75) Inventors: Thomas H. Baum, New Fairfield, CT (US); Jeffrey F. Roeder, Brookfield, CT (US); Chongying Xu, New Milford, CT (US); Bryan C. Hendrix, Danbury, CT (US)

(73) Assignee: Advanced Technology Materials, Inc., Danbury, CT (US)

(*) Notice: Subject to any disclaimer, the term of this patent is extended or adjusted under 35 U.S.C. 154(b) by 523 days.

(21) Appl. No.: 09/907,282

(22) Filed: Jul. 17, 2001

(65) Prior Publication Data

US 2002/0015790 A1 Feb. 7, 2002

Related U.S. Application Data

(63) Continuation-in-part of application No. 09/793,023, filed on Feb. 26, 2001, now Pat. No. 6,623,656, which is a continuation-in-part of application No. 09/414,133, filed on Oct. 7, 1999, now Pat. No. 6,618,173.

(51) Int. Cl.
*C23C 30/00* (2006.01)
*C23C 16/40* (2006.01)
*C07F 7/28* (2006.01)

(52) U.S. Cl. .................. 106/287.19; 556/40
(58) Field of Classification Search ............ 106/287.19; 556/40

See application file for complete search history.

(56) References Cited

U.S. PATENT DOCUMENTS

| | | | |
|---|---|---|---|
| 5,204,314 A | 4/1993 | Kirlin et al. | |
| 5,225,561 A | 7/1993 | Kirlin et al. | |
| 5,280,012 A | 1/1994 | Kirlin et al. | |
| 5,342,648 A | 8/1994 | MacKenzie | |
| 5,453,494 A | 9/1995 | Kirlin et al. | |
| 5,536,323 A | 7/1996 | Kirlin et al. | |
| 5,677,002 A | 10/1997 | Kirlin et al. | |
| 5,820,664 A | 10/1998 | Gardiner et al. | |
| 5,859,274 A | 1/1999 | Baum et al. | |
| 5,916,359 A | 6/1999 | Baum et al. | |
| 5,919,522 A | 7/1999 | Stauf et al. | |
| 6,063,639 A | 5/2000 | Kim et al. | |
| 6,080,593 A | 6/2000 | Kim et al. | |
| 6,110,529 A | 8/2000 | Gardiner | |
| 6,126,996 A * | 10/2000 | Kirlin et al. | 427/252 |
| 6,214,105 B1 * | 4/2001 | Hintermaier et al. | 106/287.19 |
| 6,316,797 B1 * | 11/2001 | Van Buskirk et al. | 257/295 |
| 6,340,386 B1 * | 1/2002 | Hendrix et al. | 106/287.18 |
| 6,344,079 B1 * | 2/2002 | Baum | 106/287.18 |
| 6,399,208 B1 * | 6/2002 | Baum et al. | 428/446 |
| 6,444,264 B1 * | 9/2002 | Hintermaier et al. | 427/255.32 |
| 6,511,706 B1 * | 1/2003 | Hendrix et al. | 427/255.32 |
| 6,562,990 B1 * | 5/2003 | St. Clair et al. | 556/40 |
| 6,599,447 B1 * | 7/2003 | Stauf et al. | 252/520.21 |
| 6,623,656 B1 * | 9/2003 | Baum et al. | 252/62.9 PZ |

FOREIGN PATENT DOCUMENTS

JP 05013676 1/1993

OTHER PUBLICATIONS

Gan, J.–Y. et al., "Dielectric property of $(TiO_2)_x$–$(Ta_2O_5)_{1-x}$ thin films," Appl. Phys. Lett. 72 (3), p. 332 (Jan. 19, 1998).
Alers, G. B. et al., "Nitrogen plasma annealing for low temperature $Ta_2O_5$ films" Appl. Phys. Lett. 72 (11), p. 1308, (Mar. 16, 1998).
Kirlin et al., "MOCVD of $BaSrTiO_3$ for ULSI DRAMS", Integrated Ferroelectrics vol. 7, p. 307 (1995).
Van Dover, R.B., "Amorphous lanthanide–doped $TiO_x$ dielectric films", Appl. Phys. Lett. 74 (20) p. 3041, (May 17, 1999).
Roy, P. K., et al., "Stacked high–ϵ gate dielectric for giga–scale integration of metal–oxide–semiconductor technologies" Appl. Phys. Lett. 72 (22) p. 2835, (Jun. 1, 1998).
Van Dover, R.B. et al., "Discovery of a useful thin–film dielectric using a composition–spread approach", Nature, vol. 392, (Mar. 12, 1998) p. 162.
Nomura, Koji et al., "Electrical properties of $Al_2O_3$–$Ta_2O_5$ composite dielectric thin films prepared by RF reactive sputtering", Solid State Tech., (Apr. 1997), p. 922.
Alers, G.B. et al., "Advanced amorphous dielectrics for embedded capacitors", IEDM, 99–797, p. 33.3.1 1999.
Kawano, H., et al, "Effects of crystallization on structural and dielectric properties of thin amorphous films of $(1-x)BaTiO_3$–$xSrTiO_3$ (x=0–0.5, 1.0)," J. Appl. Phys., 73 (10), (May 15, 1993) p. 5141.
Van Dover, R.B. et al., "Advanced dielectrics for gate oxide, DRAM and rf capacitors", IDEM 98–823, p 30.6.1 1998.
U.S. Appl. No. 09/414,133, Baum et al.
Inorganic Chemistry, (1999) vol. 38, pp. 1432–1437.
Jones, et al., "MOCVD of Zirconia Thin Films by Direct Liquid Injection Using a New Class of Zirconium Precursor", Chem. Vap. Dep., vol. 4, (1998) pp. 46–49.

* cited by examiner

*Primary Examiner*—David Brunsman
(74) *Attorney, Agent, or Firm*—Steven J. Hultquist; Intellectual Property/Technology Law; Maggie Chappuis

(57) ABSTRACT

Chemical vapor deposition (CVD) precursor compositions for forming metal oxide high dielectric constant (κ) thin films. The precursor composition in one embodiment comprises a metal precursor having a general formula M(β-diketonate)$_2$(OR)$_2$, wherein M is Hf, Zr or Ti, and R is t-butyl. The precursor composition may also comprise a solvent medium selected from the group consisting of ethers, glymes, tetraglymes, amines, polyamines, alcohols, glycols, aliphatic hydrocarbon solvents, aromatic hydrocarbon solvents, cyclic ethers, and compatible combinations of two or more of the foregoing.

63 Claims, 13 Drawing Sheets

SOURCE REAGENT COMPOSITIONS FOR CVD FORMATION OF HIGH DIELECTRIC CONSTANT AND FERROELECTRIC METAL OXIDE THIN FILMS AND METHOD OF USING SAME

BACKGROUND OF THE INVENTION

1. Filed of the Invention

The present invention relates to metal precursors useful for chemical vapor deposition (CVD) of high dielectric constant (κ) and/or ferroelectric metal oxide thin films.

2. Description of the Related Art

Zirconium and hafnium-containing silicates possess dielectric constant (κ) values in the range of from about 10 to 20, and therefore are highly useful as gate dielectric materials in various microelectronic structures and devices. Zirconium- and hafnium-containing ferroelectric or high dielectric constant complex metal oxides, such as Pb(Zr,Ti)O$_3$ or (Ba,Sr)(Zr,Ti)O$_3$, are also being considered for the manufacturing of microelectronic devices. For these latter applications dielectric constants in excess of 50 and, for ferroelectric materials, hysteresis polarization, are the properties that make these materials desirable.

In such applications, the choice of zirconium or hafnium source reagents is of critical importance for the successful chemical vapor deposition of high quality Zr/Hf-doped gate dielectric ferroelectric, or high dielectric constant metal oxide thin films.

Fabrication of high quality Zr/Hf doped gate dielectric, high dielectric constant and/or ferroelectric metal oxide thin films requires that the zirconium or hafnium CVD source reagents so employed produce a clean interface between the substrate surface and the Zr/Hf thin films deposited thereon. Deleterious occurrence of side reactions, e.g., when the substrate is silicon, produce predominantly silicon dioxide (SiO$_2$), locally doped SiO$_2$, and /or other surface impurities, are desirably minimized, because formation of such surface impurities reduces the capacitance and therefore compromises performance of the deposited gate dielectric, high dielectric constant and/or ferroelectric metal oxide thin films.

Further, the Zr/Hf source reagents must be thermally stable to avoid premature decomposition of such source reagents before they reach the CVD reaction chamber during the CVD process. Premature decomposition of source reagents not only results in undesirable accumulation of side products that will clog fluid flow conduits of the CVD apparatus, but also causes undesirable variations in composition of the deposited gate dielectric, high dielectric constant and/or ferroelectric metal oxide thin film.

Moreover, the Zr/Hf source reagents have to be chemically compatible with other source reagents used in the CVD process. "Chemically compatible" means that the Zr/Hf source reagents will not undergo undesirable side reactions with other source reagents, e.g., reagents containing silicon or other metals, such as Pb and/or Ti.

Finally, the Zr/Hf source reagents must be able to maintain their chemical identity over time when dissolved or suspended in organic solvents. Any change in chemical identity of source reagents in the solvent medium is deleterious since it impairs the ability of the CVD process to achieve repeatable delivery and film growth.

There is a continuing need in the art to provide improved Zr/Hf source reagents suitable for high efficiency CVD processes, for fabricating corresponding high quality Zr/Hf-doped gate dielectric, high dielectric constant and/or ferroelectric metal oxide thin films.

SUMMARY OF THE INVENTION

The present invention broadly relates to source reagent compositions having utility for forming dielectric thin films such as doped gate dielectrics, high dielectric constant metal oxides and/or ferroelectric metal oxides, and to a chemical vapor deposition (CVD) method for deposition of metal containing thin films utilizing such composition.

The invention in one aspect relates to source reagent composition of the formula:

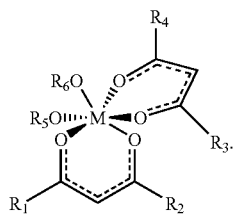

In such formula, M denotes zirconium (Zr), hafnium (Hf) or titanium (Ti). Each of $R_1$, $R_2$, $R_3$, and $R_4$ is independently selected (i.e., it can either be the same as or different from other(s) of the $R_1$, $R_2$, $R_3$, and $R_4$ substituents) from the group consisting of H, aryl, perfluoroaryl, $C_1$–$C_8$ alkyl, and $C_1$–$C_8$ perfluoroalkyl. $R_5$ and $R_6$ are both tert-butyl (tBu).

As used herein, the term "thin film" refers to a material layer having a thickness of less than about 1000 microns.

In a specific aspect of the present invention, the metal precursor comprises at least one β-diketonate moiety. Illustrative β-diketonate moieties include the following:

| β-diketonate moiety | abbreviation |
|---|---|
| 2,4-pentanedione | acac; |
| 1,1,1-trifluoro-2,4-pentanedionato | tfac; |
| 1,1,1,5,5,5-hexafluoro-2,4-pentanedionato | hfac; |
| 2,2,6,6-tetramethyl-3,5-heptanedionato | thd; |
| 2,2,7-trimethyl-3,5-octanedionato | tod; |
| 6,6,7,7,8,8,8-heptafluoro-2,2-dimethyl-3,5-octanedionato | fod. |

One particularly preferred metal precursor species of the present invention has the formula M(thd)$_2$(O-tBu)$_2$ wherein M is Zr, Hf or Ti. In such precursor, the bulky t-butyl groups function to minimize deleterious isomerization reactions and enhance thermal stability of the precursor. The preferred M(thd)$_2$(O-tBu)$_2$ precursor can be synthesized by reacting M(O-tBu)$_4$ with two equivalents of Hthd in a dry hydrocarbon or aryl solvent according to the following equation:

$$M(O\text{-}tBu)_4 + 2Hthd \rightarrow M(thd)_2(O\text{-}tBu)_2 + 2HO\text{-}tBu \qquad (1)$$

Another aspect of the present invention relates to a CVD source reagent composition comprising a metal precursor as described hereinabove, and a solvent medium in which the metal precursor is soluble or suspendable. Providing a source reagent composition in liquid (e.g., solution or suspension) form facilitates rapid volatilization (e.g., flash vaporization) of the source reagent composition and transport of the resultant precursor vapor to a deposition locus such as a CVD reaction chamber. Further, when used in solution the precursor stability is greatly improved over other prior art alkoxide analogs.

The solvent medium utilized in the CVD source reagent composition may comprise any suitable solvent species, or combination of solvent species, with which the metal precursor(s) are compatible. Such solvent medium may for example comprise ethers, glymes, tetraglymes, amines, polyamines, aliphatic hydrocarbon solvents, aromatic hydrocarbon solvents, cyclic ethers, or compatible combinations of two or more of the foregoing solvents.

A particularly preferred solvent species useful in the practice of the present invention is octane.

In yet another aspect, the invention relates to a method of forming a metal containing dielectric thin film on a substrate, wherein the dielectric thin film is selected from the group consisting of doped gate dielectric, high dielectric constant metal oxide and ferroelectric metal oxide, comprising the following steps:

vaporizing a source reagent composition comprising a metal precursor to form a source reagent precursor vapor;

transporting such source reagent precursor vapor into a chemical vapor deposition zone, optionally using a carrier gas;

contacting the substrate with the source reagent vapor in the chemical vapor deposition zone in the presence of an oxidizer and at elevated temperature, to deposit a corresponding metal-containing thin film on the substrate, e.g., a doped gate dielectric thin film, a high dielectric constant metal oxide thin film and/or a ferroelectric metal oxide thin film;

wherein the metal precursor has the following formula:

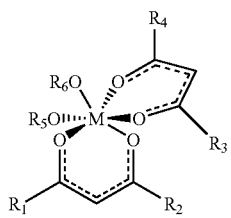

wherein:

M is Zr, Hf or Ti;

each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and $R_5$ and $R_6$ are both t-butyl groups.

The step of vaporizing the source reagent composition comprising the metal precursor is preferably carried out at a vaporization temperature in the range of from about 100° C. to about 300° C. Within this narrow range of vaporization temperature, the metal precursor is effectively vaporized with a minimum extent of premature decomposition.

In the optional use of a carrier gas in the practice of the present invention, for transporting the vaporized source reagent composition into the chemical vapor deposition zone, suitable carrier gas species include gases that do not adversely affect the metal-containing film being formed on the substrate. Preferred gases include argon, helium, krypton or other inert gas, with helium and argon gas generally being most preferred. In one illustrative embodiment, helium or argon gas may be introduced for mixing with the vaporized source reagent composition at a flow rate of about 100 standard cubic centimeters per minute (sccm).

Oxidizers useful for the broad practice of the present invention include, but are not limited to, $O_2$, $N_2O$, and $O_3$.

More preferably, the oxidizer used comprises oxygen, and in one illustrative embodiment corresponding to the helium or argon flow rate illustratively described above, oxygen is introduced into the chemical vapor deposition zone at a flow rate of about 700 sccm.

The deposition of the metal-containing dielectric thin film is preferably carried out under an elevated deposition temperature in a range of from about 300° C. to about 750° C.

Other aspects, features, and embodiments of the invention will be more fully apparent from the ensuing disclosure and appended claims.

DETAILED DESCRIPTION OF THE INVENTION AND PREFERRED EMBODIMENTS THEREOF

Figure 1:
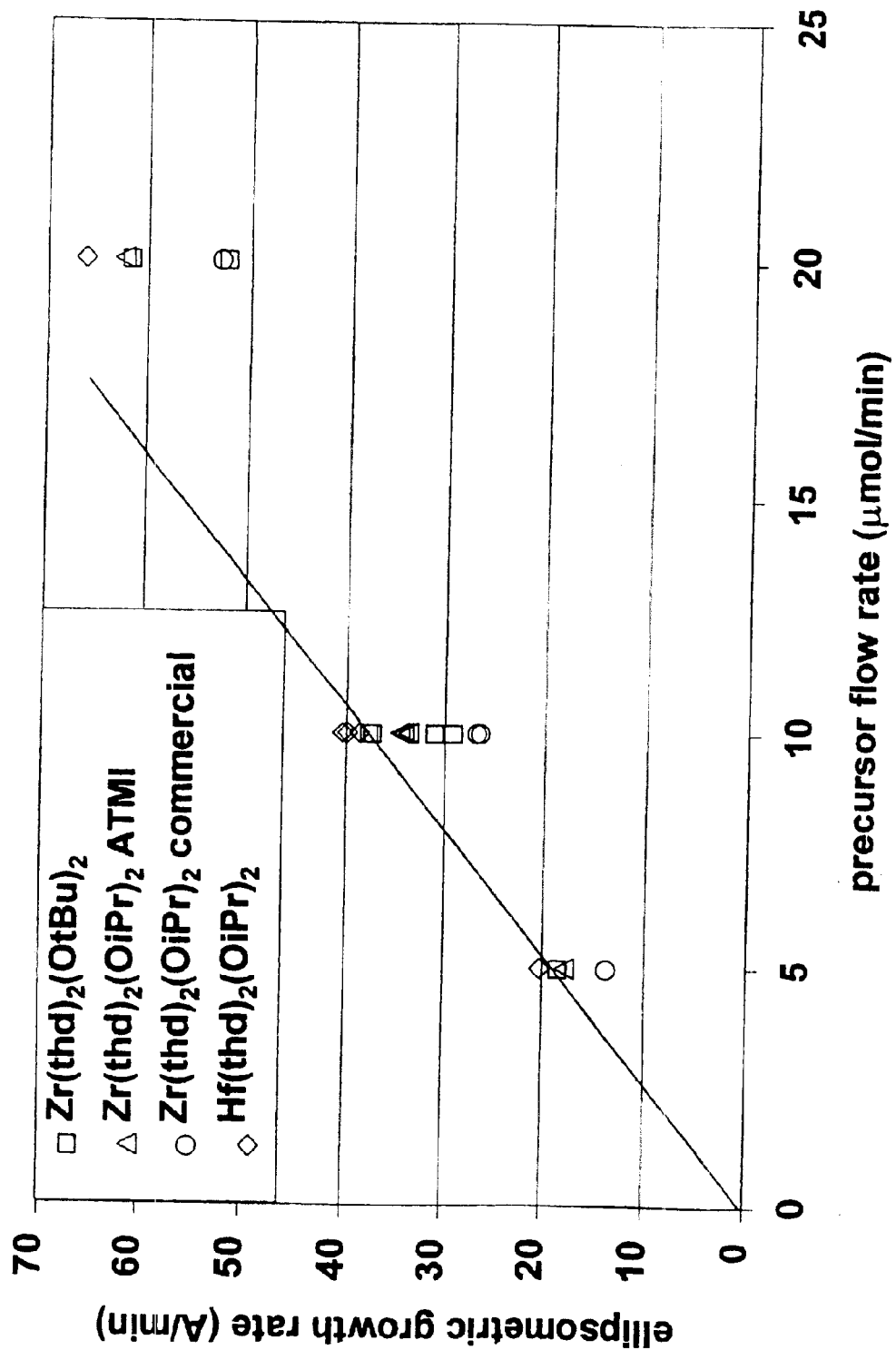
FIG. 1 is a comparative plot of film growth rates calculated from ellipsometric measurements, as a function of precursor flow rate, for various Zr or Hf metal precursors.

The disclosure of the following United States patents and patent applications are hereby incorporated by reference in their respective entireties:

U.S. patent application Ser. No. 09/726,183 filed Nov. 29, 2000 in the names of Gregory T. Stauf, et al.;

U.S. patent application Ser. No. 09/469,700 filed Dec. 22, 1999 in the name of Bryan C. Hendrix;

U.S. patent application Ser. No. 09/414,133 filed Oct. 7, 1999 in the names of Thomas H. Baum, et al.;

U.S. patent application Ser. No. 09/251,890 filed Feb. 19, 1999 in the names of Peter C. Van Buskirk, et al.;

U.S. patent application Ser. No. 09/026,946 filed Feb. 28, 1998 in the names of Jeffrey R. Roeder, et al.;

U.S. patent application Ser. No. 08/835,768 filed Apr. 8, 1997 in the names of Thomas H. Baum, et al., and issued Jul. 6, 1999 as U.S. Pat. No. 5,919,522;

U.S. patent application Ser. No. 08/484,654 filed Jun. 7, 1995 in the names of Robin A. Gardiner et al., and issued Aug. 29, 2000 as U.S. Pat. No. 6,110,529;

U.S. patent application Ser. No. 08/414,504 filed Mar. 31, 1995 in the names of Robin A. Gardiner et al., and issued Oct. 13, 1998 as U.S. Pat. No. 5,820,664;

U.S. patent application Ser. No. 08/280,143 filed Jul. 25, 1994 in the names of Peter S. Kirlin, et al., and issued Jul. 16, 1996 as U.S. Pat. No. 5,536,323;

U.S. patent application Ser. No. 07/807,807 filed Dec. 13, 1991 in the names of Peter S. Kirlin, et al., and issued Apr. 20, 1993 as U.S. Pat. No. 5,204,314;

U.S. patent application Ser. No. 08/181,800 filed Jan. 15, 1994 in the names of Peter S. Kirlin, et al., and issued Sep. 26, 1995 as U.S. Pat. No. 5,453,494;

U.S. patent application Ser. No. 07/918,141 filed Jul. 22, 1992 in the names of Peter S. Kirlin, et al., and issued Jan. 18, 1994 as U.S. Pat. No. 5,280,012; and U.S. patent application Ser. No. 07/581,631 filed Sep. 12, 1990 in the names of Peter S. Kirlin, et al., and issued Jul. 6, 1993 as U.S. Pat. No. 5,225,561.

The above-identified applications and patents variously describe source reagent compositions, their synthesis and formulations, thin film compositions, as well as CVD techniques including liquid delivery CVD, and provide background information with respect to the present invention.

On fundamental grounds, the compounds of the present invention would not be expected to be suitable for use as advantageous source reagents for depositing dielectric thin films, e.g., by CVD, since compounds of the general formula M(thd)$_2$(O-iPr)$_2$ (wherein "thd" denotes 2,2,6,6-tetramethyl-3,5-heptanedionato, and "i-Pr" denotes isopropyl) are known to be highly susceptible to cis- to trans- equilibration, dimerization and deleterious proportionation reactions, resulting in an alteration of the chemical identity of such compounds including the formation of dinuclear species, such as [M(thd)$_2$(O-iPr)$_2$]$_2$, particularly in organic solvent medium. See INORGANIC CHEMISTRY, 1999, 38, 1432–1437;

In contrast to such expectation, the metal source reagent compounds of the invention have been found to be surprisingly stable, even in organic solutions, while at the same time they are volatilizable at low temperatures that are consistent with efficient chemical vapor deposition processing.

The metalorganic compounds of the present invention have a general formula M(β-diketonate)$_2$(O-tBu)$_2$. Compounds of such general type have the following structure:

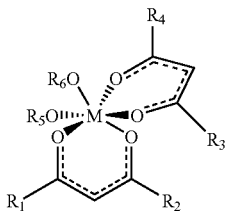

wherein M is Zr, Hf or Ti; each of R$_1$, R$_2$, R$_3$, and R$_4$ is independently selected from the group consisting of H, aryl, perfluoroaryl, C$_1$–C$_8$ alkyl, and C$_1$–C$_8$ perfluoroalkyl; and R$_5$ and R$_6$ are both t-butyl groups.

The presence of the bulky t-butyl group in the alkoxide ligands limits the occurrence of cis- to trans- equilibration and eliminates the proportionation to dinuclear species over time, particularly when the compound is in an organic solution or suspension. Such M(β-diketonate)$_2$(O-tBu)$_2$ compounds are very stable chemically in organic solutions and also possess the following advantageous features: good deposition rates; good thermal stability; higher elemental purity; formation of practically carbon-free films (in contrast to the reported literature, e.g. Jones, et al., "MOCVD of Zirconia Thin Films by Direct Liquid Injection Using a New Class of Zirconium Precursor", *Chem. Vap. Dep.*, Vol. 4, 1998, PP. 46–49.); compatibility in solvent media with a variety of other alkoxide/beta-diketonate precursors and/or beta-diketonate precursors for various transition metals and alkali earth metals; ready decomposition at CVD process temperatures; and good solubility in a wide variety of organic solvents and solvent media.

The β-diketonate ligand(s) in the M(β-diketonate)$_2$(O-tBu)$_2$ compound may be of any suitable type. The β-diketonate ligands in the compound may be the same as or different from one another. Illustrative β-diketonate ligands include the following:

| β-diketonate ligand | abbreviation |
|---|---|
| 2,4-pentanedione | acac; |
| 1,1,1-trifluoro-2,4-pentanedionato | tfac; |
| 1,1,1,5,5,5-hexafluoro-2,4-pentanedionato | hfac; |
| 2,2,6,6-tetramethyl-3,5-heptanedionato | thd; |
| 2,2,7-trimethyl-3,5-octanedionato | tod; |
| 6,6,7,7,8,8-heptafluoro-2,2-dimethyl-3,5-octanedionato | fod. |

Particularly preferred β-diketonate ligands of the metal source reagent compounds of the invention include 2,2,6,6-tetramethyl-3,5-heptanedionato (thd). M(thd)$_2$(O-tBu)$_2$ compounds have high film growth rates and are easily prepared in large quantities and at high purity, as Zr, Hf and Ti metal precursors for CVD processes.

Figure 2:
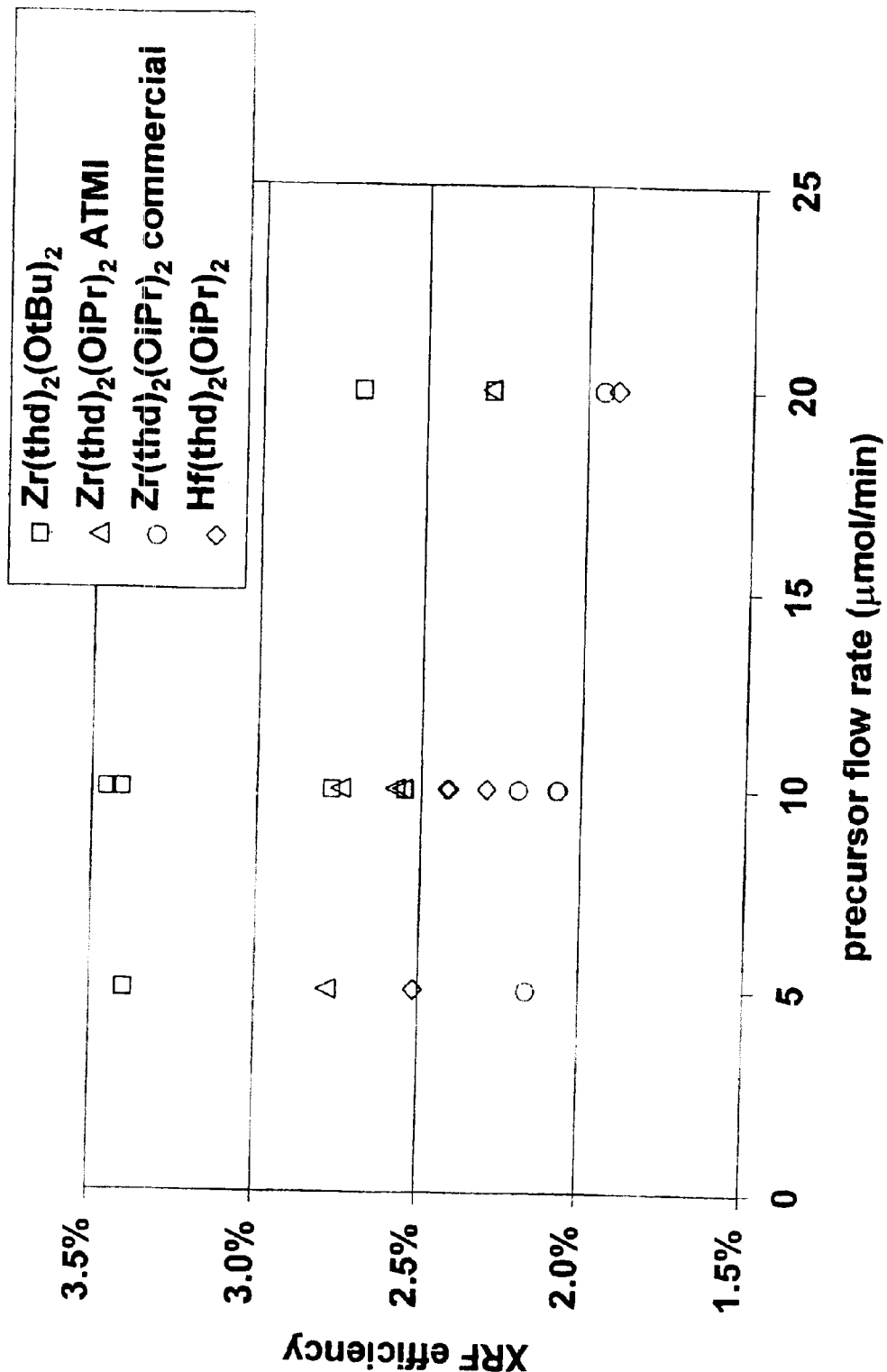
FIG. 2 is a comparative plot of incorporation efficiency of precursors measured using x-ray fluorescence (XRF) technique, as a function of precursor flow rate, for various Zr or Hf metal precursors.

FIGS. 1 and 2 compare film growth rates and efficiency of four metal precursors: Zr(thd)$_2$(O-iPr)$_2$ (supplied commercially and labeled as "commercial"), Zr(thd)$_2$(O-iPr)$_2$ (synthesized in house at ATMI and labeled "ATMI"), Zr(thd)$_2$(O-tBu)$_2$, and Hf(thd)$_2$(O-iPr)$_2$. For each precursor, a minimum of five films was grown at three different precursor delivery rates according to the following order: 0.10, 0.05, 0.10, 0.20, and 0.10 ml/min. The film growth time was varied to maintain a constant 100 μmol of precursor delivery amount during each cycle of growth.

In FIG. 1, film thickness of each film so deposited was measured using single-wavelength ellipsometry at 70° C. incidence angle.

In FIG. 2, the film thickness was measured using x-ray fluorescence (XRF). For ZrO$_2$ films, the XRF was calibrated by using the densest films measured by ellipsometry. For HfO$_2$, the XRF was calibrated by assuming that the x-ray efficiencies of such films were equivalent to TaO$_{2.5}$.

FIGS. 1 and 2 show that Zr(thd)$_2$(O-tBu)$_2$ has the highest growth rate among the Zr metal precursors.

Figure 3:
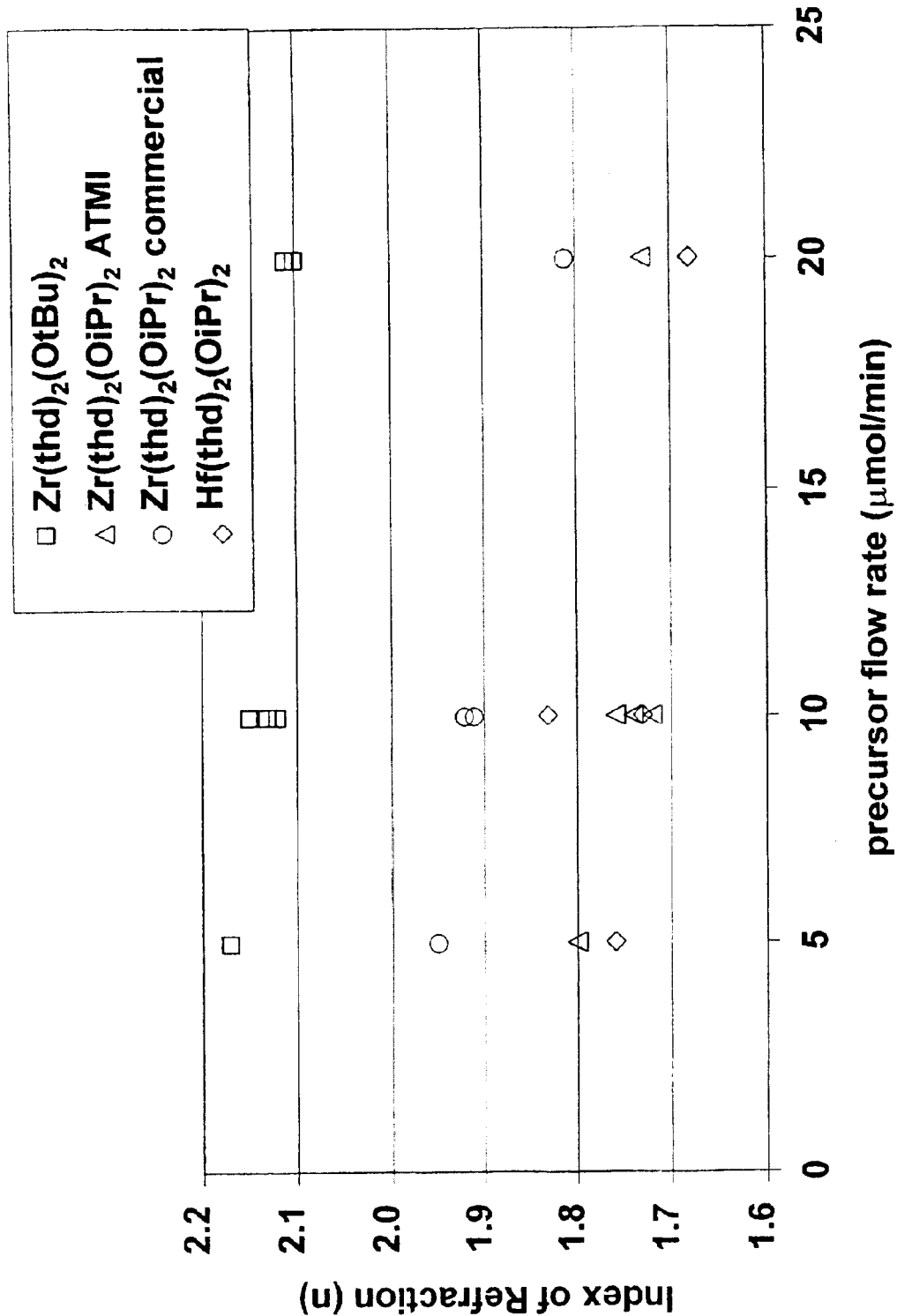
FIG. 3 is a comparative plot of index of refraction measured for various Zr or Hf metal precursors as a function of precursor flow rate.

FIG. 3 compares index of refraction for films deposited from the same four metal precursors Zr(thd)$_2$(O-iPr)$_2$ (commercial), Zr(thd)$_2$(O-iPr)$_2$ (ATMI), Zr(thd)$_2$(O-tBu)$_2$, and Hf(thd)$_2$(O-iPr)$_2$, at similar precursor delivery rates. FIG. 3 shows that Zr(thd)$_2$(O-tBu)$_2$ forms the densest ZrO$_2$ film, as indicated by its highest index of refraction.

The composition of ZrO$_2$ films formed by Zr(thd)$_2$(O-iPr)$_2$, Zr(thd)$_2$(O-tBu)$_2$, and Hf(thd)$_2$(O-tBu)$_2$ was analyzed by x-ray photoelectron spectroscopy (XPS) after sputtering the surface layers of the ZrO$_2$ films away to determine the carbon contamination within the bulk film. The XPS results show that the carbon levels of films formed using Zr(thd)$_2$(O-tBu)$_2$ precursor were below reliable detection range of the XPS. In contrast, carbon levels of films formed by Zr(thd)$_2$(O-iPr)$_2$ precursor were above such detection range. This indicates that Zr(thd)$_2$(O-tBu)$_2$ is capable of forming carbon-free ZrO$_2$ thin films and reduce carbon contaminants to a lower level than that of films formed by Zr(thd)$_2$(O-iPr)$_2$.

The metal precursors of the invention are usefully employed in a method of forming metal containing high dielectric constant metal oxide and ferroelectric metal oxide thin films on a substrate, wherein the dielectric thin film is selected from the group consisting of:

PbTiO$_3$,
PbZrO$_3$ and
PbZr$_x$Ti$_{1-x}$O$_3$, wherein x=0 to 1,
Ba$_y$/Sr$_{1-y}$Zr$_x$Ti$_{1-x}$O$_3$ wherein x=0 to 1 and y=0 to 1 Hf$_{2x}$Ta$_{2-2x}$O$_{5-x}$ $Zr_{2x}Ta_{2-2x}O_{5-x}$
$Hf_{2x}Nb_{2-2x}O_{5-x}$
$Zr_{2x}Nb_{2-2x}O_{5-x}$
$(Zr,Hf)_{2x}(Nb,Ta)_{2-2x}O_{5-x}$
All with $0.05 < x < 0.95$ (5–95% Zr or Hf)
$Hf_{2x}Bi_{2-2x}O_{3+x}$
$Zr_{2x}Bi_{2-2x}O_{3+x}$
$(Zr,Hf)_{2x}Bi_{2-2x}O_{3+x}$
With $0.4 < x < 0.95$ (40–95% Zr or Hf)
$Hf_{2x}L_{2-2x}O_{3+x}$
$Zr_{2x}L_{2-2x}O_{3+x}$
$(Zr,Hf)_{2x}L_{2-2x}O_{3+x}$
Where L is from the lanthanide series of elements and with $0.05 < x < 0.95$ (5–95% Zr or Hf)
$L_{2y}Hf_{2x}Ta_{2-2y-2x}O_{5-x-2y}$
$L_{2y}Zr_{2x}Ta_{2-2y-2x}O_{5-x-2y}$
$L_{2y}Hf_{2x}Nb_{2-2y-2x}O_{5-x-2y}$
$L_{2y}Zr_{2x}Nb_{2-2y-2x}O_{5-x-2y}$
$L_{2y}(Zr,Hf)_{2x}(Nb,Ta)_{2-2y-2x}O_{5-x-2y}$
Where L is from the lanthanide series of elements and with $0.05 < x < 0.90$ (5–90% Zr or Hf) and $0.05 < y < 0.90$ (5–90% Lanthanide).

Such method includes the steps of:

vaporizing a source reagent composition comprising a metal precursor to form a source reagent vapor;

transporting such source reagent vapor into a chemical vapor deposition zone containing a substrate, optionally using a carrier gas to effect such transport;

contacting the source reagent vapor with a substrate in such chemical vapor deposition zone in the presence of an oxidizer and at elevated temperature to deposit a corresponding metal-containing dielectric material on the substrate, e.g., a $PbTiO_3$, $PbZrO_3$ and $PbZr_xTi_{1-x}O_3$, wherein $x=0$ to 1 wherein the metal precursor has the following formula:

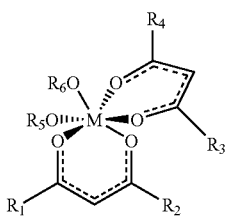

wherein:

M is Zr, Hf or Ti;

each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and $R_5$ and $R_6$ are both t-butyl groups.

As used herein, the term lanthanide series of elements is defined as lanthanum, cerium, praseodymium, neodymium, promethium, samarium, europium, gadolinium, terbium, dysprosium, holmium, erbium, thulium, ytterbium, and lutetium The source reagent composition of the present invention may comprise any suitable solvent medium that is compatible with the metal precursors contained therein. The solvent medium in such respect may comprise a single component solvent, or alternatively a solvent mixture or solution. Illustrative solvent media that may be variously usefully employed include ethers, glymes, tetraglymes, amines, polyamines, aliphatic hydrocarbon solvents, aromatic hydrocarbon solvents, cyclic ethers, and compatible combinations of two or more of the foregoing.

In one preferred embodiment of the present invention, where the precursor solution contains a silicon precursor as in the deposition of a gate dielectric, the metal precursor or precursors are dissolved in octane at a concentration of from about 0.05M to about 0.2 M. In another preferred embodiment, the metal precursor solution is delivered to vaporization chamber at a delivery rate of from about 0.05 ml/min to about 0.20 ml/min.

The precursor solutions of the present invention may further comprise chemically compatible precursors e.g., compatible polyamine-stabilized precursors such as $Pb(thd)_2pmdeta$, (where pmdeta represents pentamethyldiethylenetriamine) $Ba(thd)_2$-pmdeta, $Sr(thd)_2$-pmdeta or $Bi(thd)_3pmdeta$. "Chemically compatible" means that the source reagents will not undergo, undesirable side reactions with other co-deposited source reagents, and/or deleterious ligand exchange reactions that may alter the precursor properties, such as transport behavior, incorporation rates and film stoichiometries.

In one embodiment of the present invention, the precursor solution may further comprise compatible precursors such as $Pb(thd)_2pmdeta$ as in PZT, $Ba(thd)_2$-pmdeta, and $Sr(thd)_2$-pmdeta as in BSZT or $Bi(thd)_3pmdeta$ and the metal precursor or precursors are dissolved in an octane-polyamine mixture at a concentration of from about 0.05M to about 0.60 M. In another preferred embodiment, the metal precursor solution is delivered to vaporization chamber at a delivery rate of from about 0.05 ml/min to about 0.50 ml/min.

The present invention is also useful for depositing high dielectric constant amorphous mixed transition metal oxides, e.g., BiHfO. In one embodiment, the invention relates to a precursor solution comprising $Hf(thd)_2(O-tBu)_2$ and $Bi(thd)_3pmdeta$ dissolved in a butyl acetate-polyamine mixture.

The step of vaporizing the source reagent composition containing metal precursor is preferably carried out at a vaporization temperature in the range from about 100° C. to about 300° C. Within this narrow range of vaporization temperature, the metal precursor is effectively vaporized with a minimum extent of premature decomposition.

Vaporization of the source reagent composition may be carried out in any suitable manner and using any suitable vaporization means to form corresponding source reagent vapor for contacting with the elevated temperature substrate on which the Zr/Hf doped gate dielectric, high dielectric constant and/or ferroelectric metal oxide thin film is to be formed. The vaporization may for example be carried out with a liquid delivery vaporizer unit of a type as commercially available from Advanced Technology Materials, Inc. (Danbury, Conn.) under the trademark VAPORSOURCE, in which precursor liquid is discharged to a heated vaporization element, such as a porous sintered metal surface, and flash vaporized.

Preferably, a carrier gas is employed in the practice of the present invention for transporting the vaporized source reagent composition into the chemical vapor deposition chamber. Suitable carrier gas species include, without limitation, helium, nitrogen, krypton, argon gas, or other preferably inert gas that does not deleteriously affect the composition, formation or characteristics of the zirconium-, titanium- or hafnium-containing film being formed on the substrate. By way of example, an argon carrier gas may be employed to form a multicomponent gas stream containing the precursor vapor and the carrier gas. In a specific embodiment, such argon gas may be introduced for mixing with the vaporized source reagent composition at a flow rate of about 100 sccm. Oxidizers useful for the broad practice of the present invention include, but are not limited to, $O_2$, $N_2O$, and $O_3$. Oxygen is a preferred oxidizer species, and in a specific embodiment may be introduced into the chemical vapor deposition chamber at a flow rate of about 700 sccm.

The deposition of the high dielectric constant and or ferroelectric metal oxide material is preferably carried out at an elevated deposition temperature in a range of from about 300° C. to about 750° C. The deposition zone may comprise a CVD reactor of any suitable type and conformation, as desirable in a given end use application of the invention.

The features, aspects, and advantages of the present invention are more fully shown with reference to the following non-limiting example.

EXAMPLES

NMR Characterization of Cis- and Trans- Equilibration of $Zr(thd)_2(O-iPr)_2$

Figure 4A:
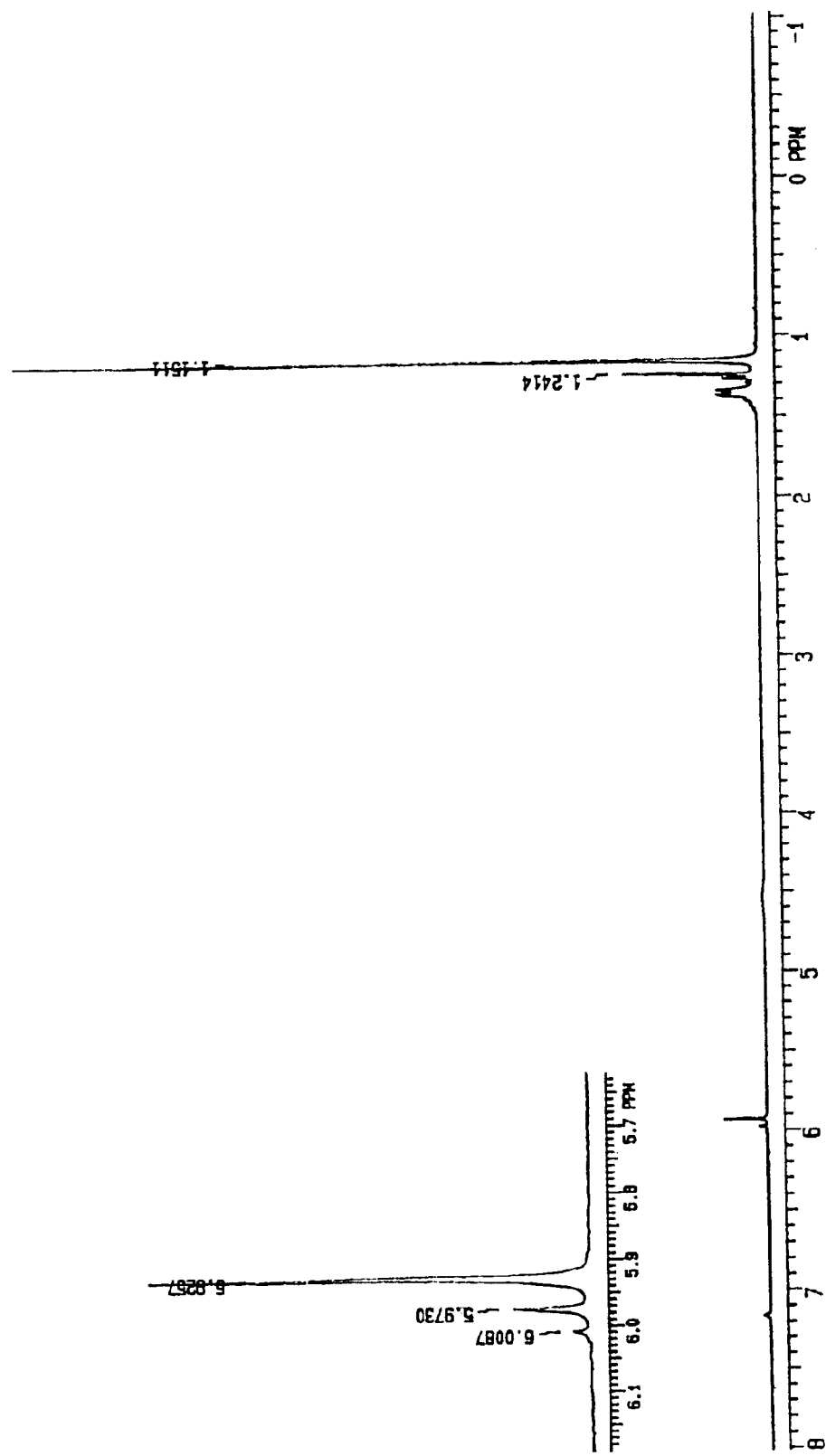
FIGS. 4a–4c are nuclear magnetic resonance (NMR) spectra of $Zr(thd)_2(O-iPr)_2$ in $C_6D_6$ showing cis- and trans- isomers equilibration over time.
Figure 4B:
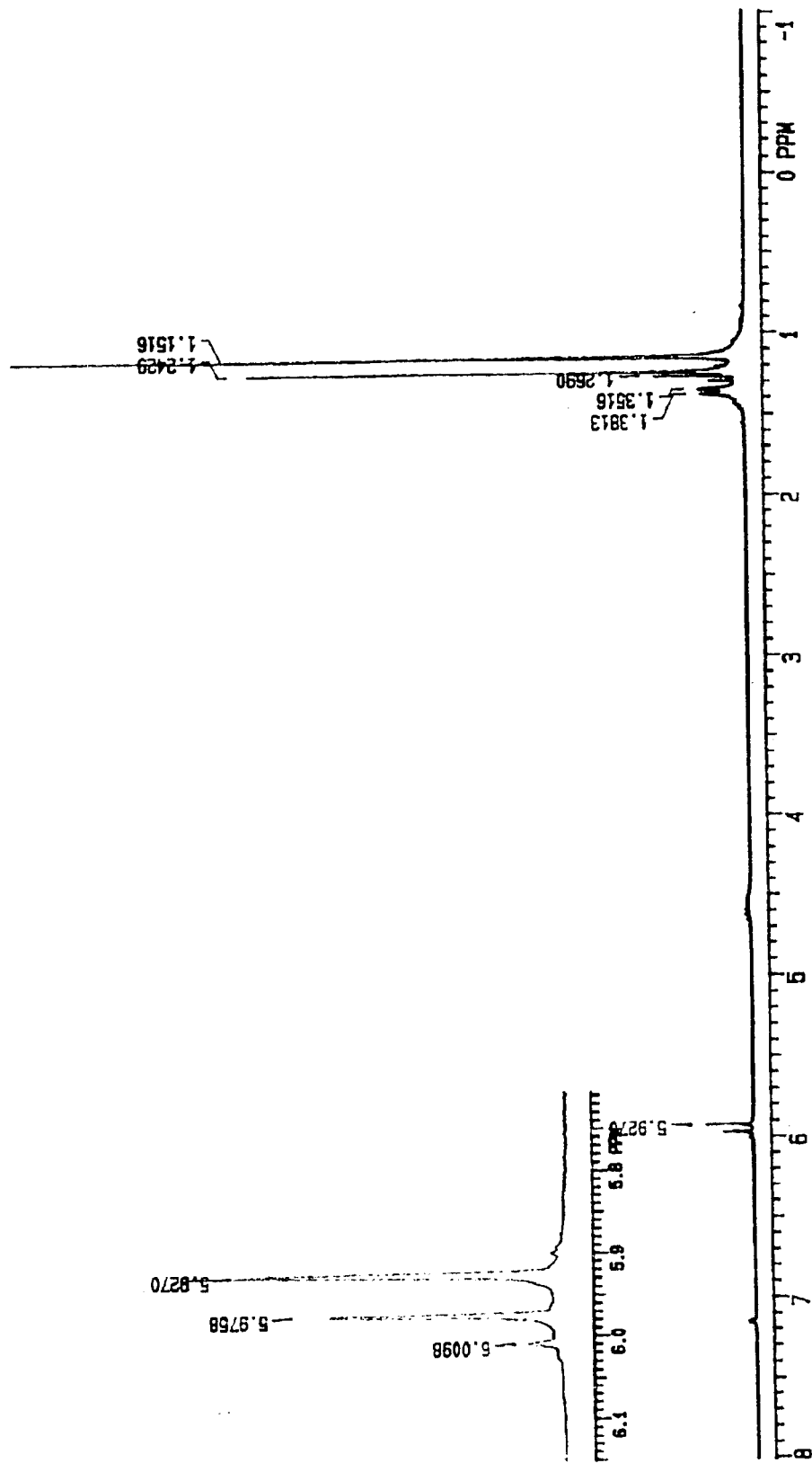
Figure 4C:
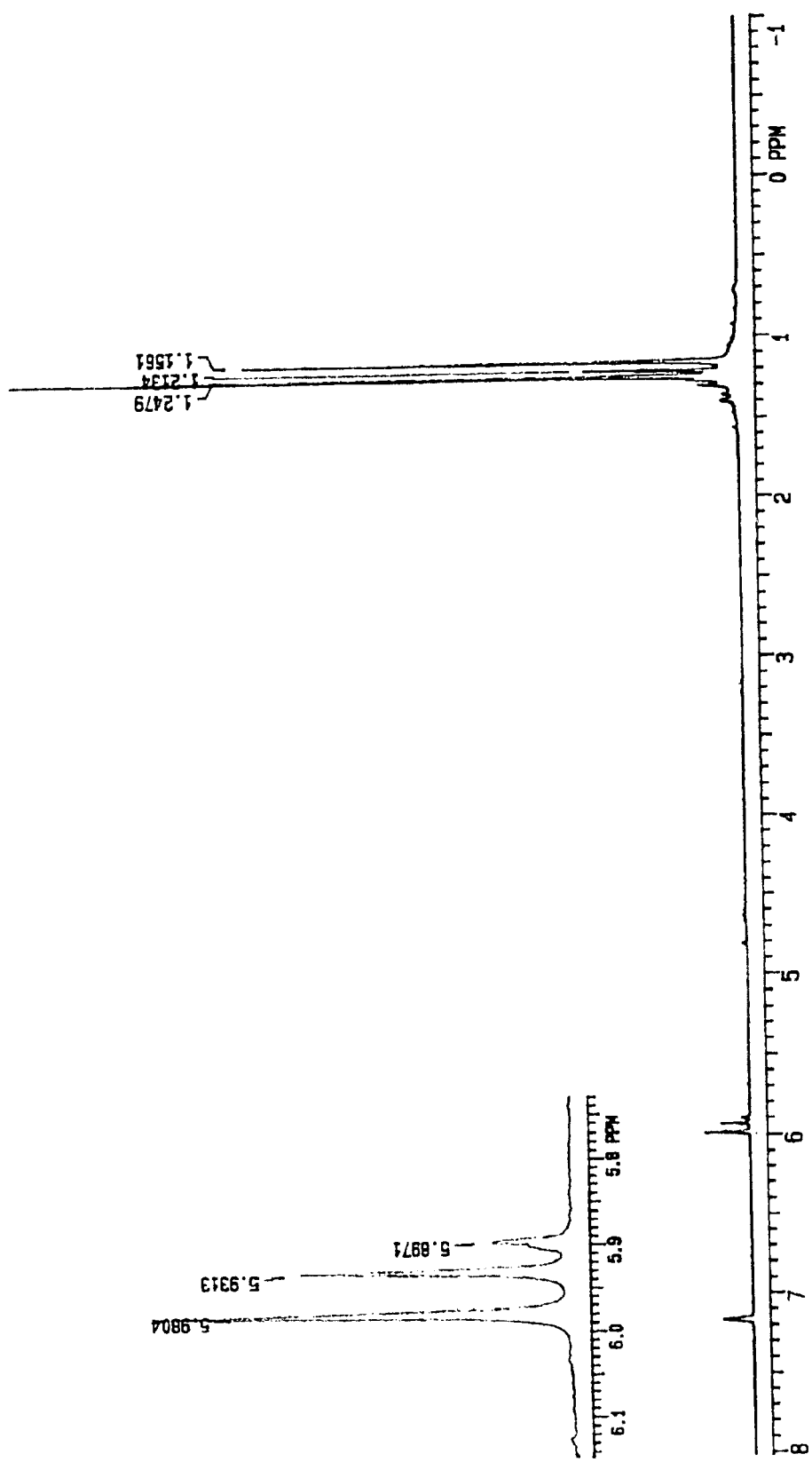

A sample of $Zr(thd)_2(O-iPr)_2$ is dissolved in deuterated benzene solvent. FIGS. 4a–4c, show the $-^1H$ NMR ($C_6D_6$), δ (ppm), spectra of a single sample of $Zr(thd)_2(O-iPr)_2$ over a period of approximately fourteen days. The original sample in FIG. 4a shows the majority of the compound to be in the cis-phase 1.15 (s, 36H=4×—C(C$\underline{H}_3$)$_3$ of thd ligands) and 5.92 (s, 2H=2×C$\underline{H}$ of thd ligands) with a detectable amount of the trans-isomer at 1.24 (s, 36H=4×—C(C$\underline{H}_3$)$_3$ of thd ligands) and 5.97 (s, 2H=2×C$\underline{H}$ of thd ligands). FIGS. 4b–4c further evidence the cis- to trans-equilibration of the sample over time as the peaks at 1.24(s, 36H=4×—C(C$\underline{H}_3$)$_3$ of thd ligands) and 5.97 (s, 2H=2×C$\underline{H}$ of thd ligands) increase over the fourteen-day period (FIG. 4b time lapse=4 days, FIG. 4c time lapse=14 days). Such isomerization is accompanied by a disproportionation/dimerization reaction, leading to a less volatile, less soluble dinuclear species of Zr, making it less desirable for CVD applications.

NMR Characterization of Cis- and Trans-Equilibration of $Hf(thd)_2(O-iPr)_2$

Figure 5A:
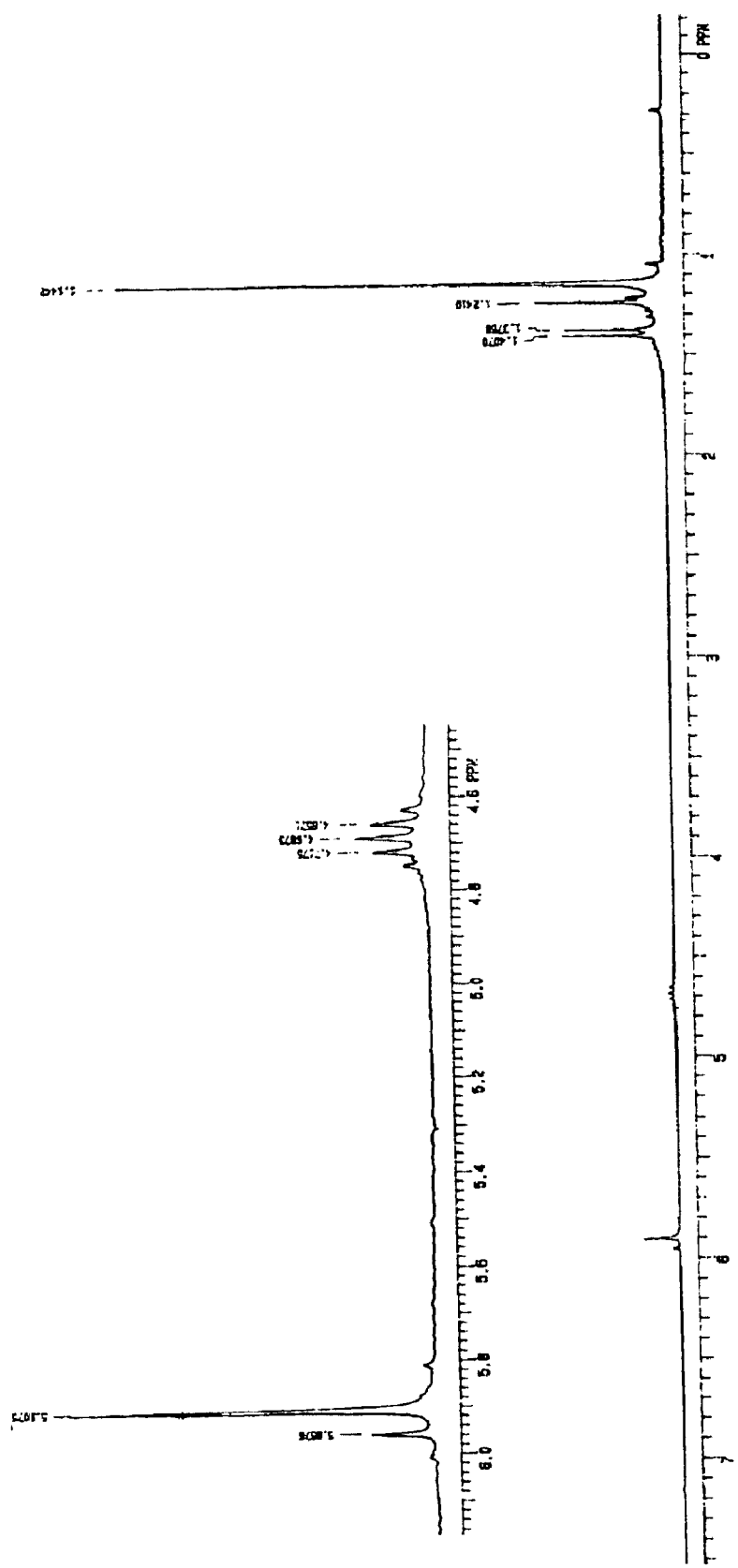
FIGS. 5a–5c are nuclear magnetic resonance (NMR) spectra of $Hf(thd)_2(O-iPr)_2$ in $C_6D_6$ showing cis- and trans- isomers equilibration over time.
Figure 5B:
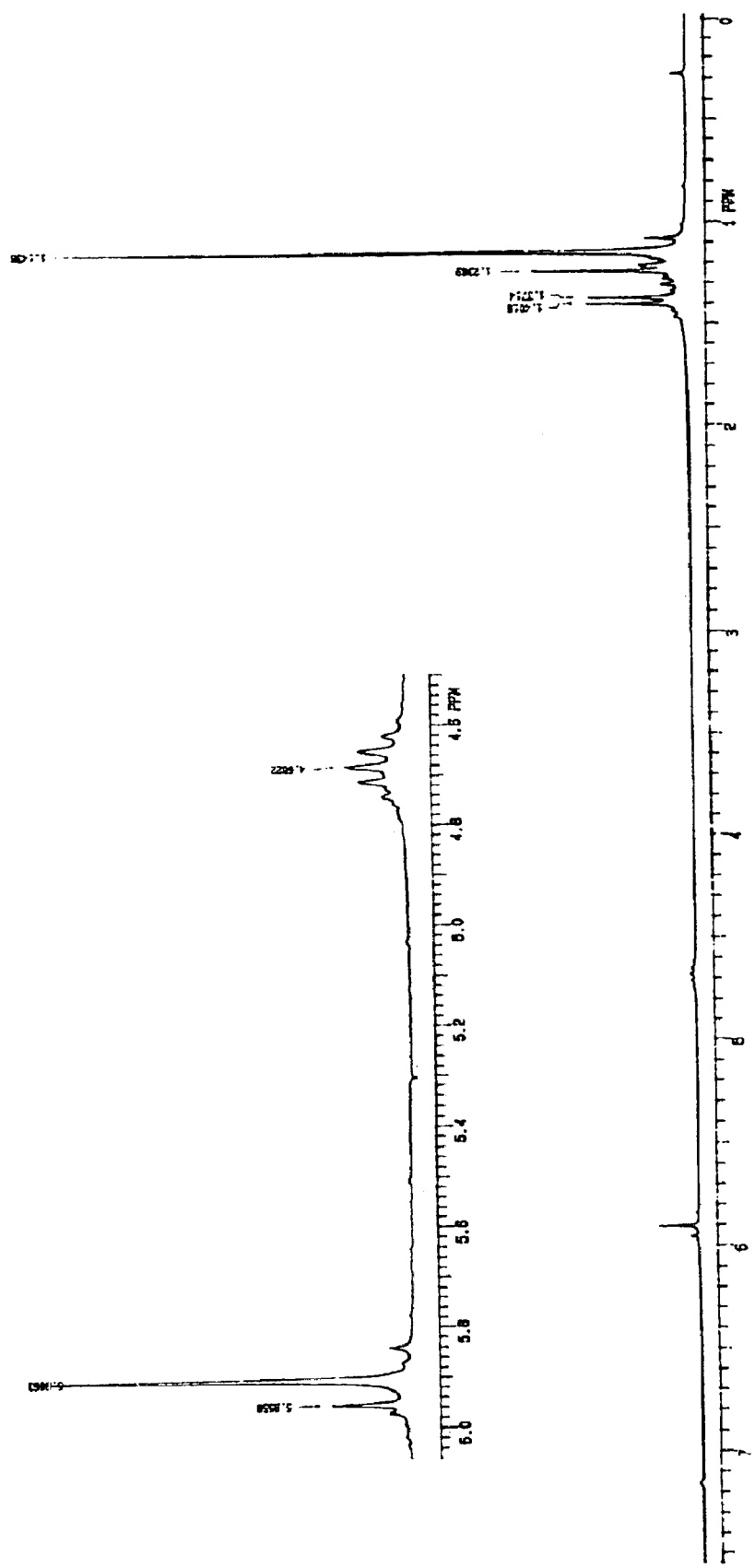
Figure 5C:
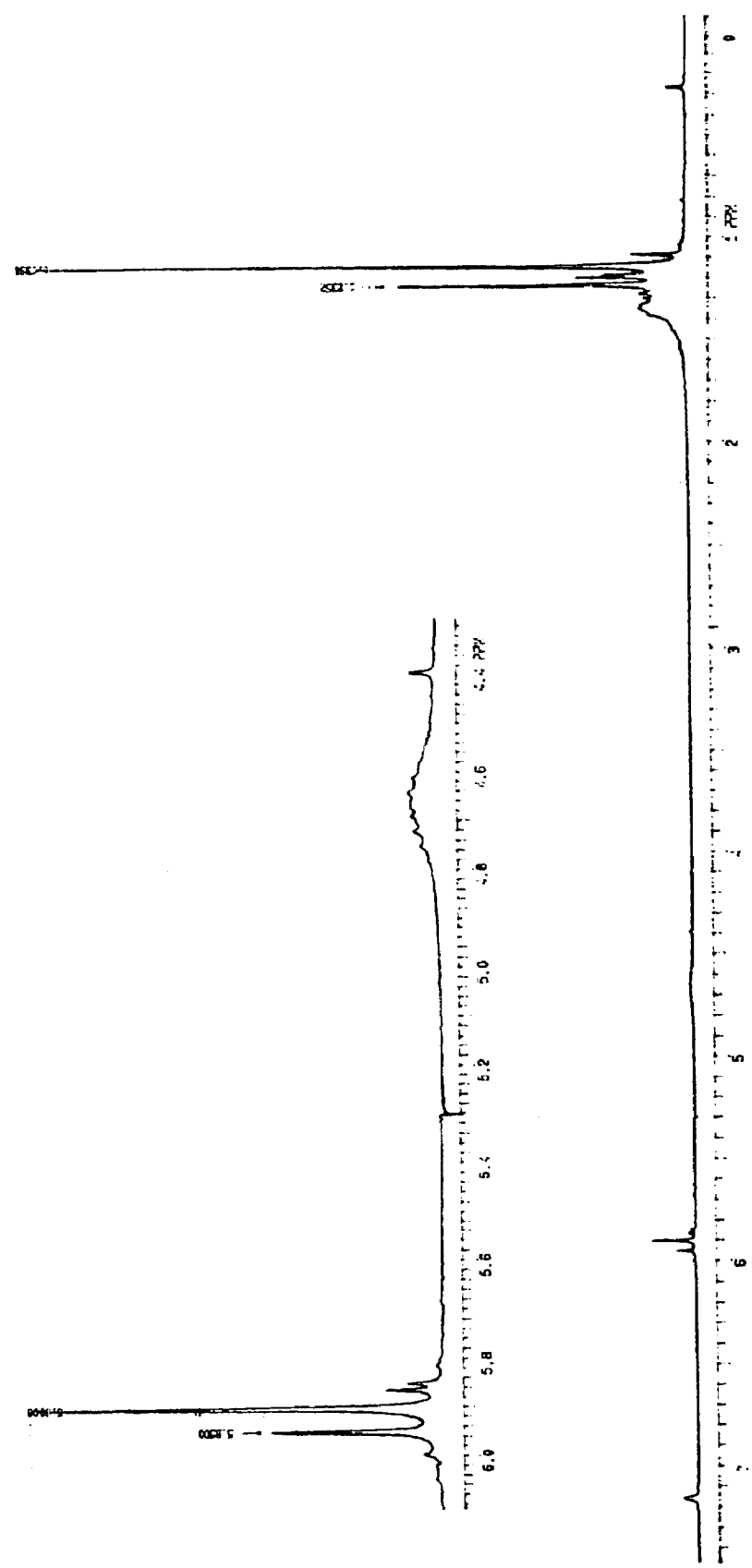

A sample of $Hf(thd)_2(O-iPr)_2$ is dissolved in deuterated benzene solvent. FIGS. 5a–5c, show the $-^1H$ NMR ($C_6D_6$), δ (ppm) spectra of a single sample of $Hf(thd)_2(O-iPr)_2$ over a period of approximately nine days. The original sample in FIG. 5a shows the majority of the compound to be in the cis-phase 1.14 (s, 36H=4×—C(C$\underline{H}_3$)$_3$ of thd ligands) and 5.91 (s, 2H=2×C$\underline{H}$ of thd ligands) with a detectable amount of the trans-isomer at 1.24 (s, 36H=4×—C(C$\underline{H}_3$)$_3$ of thd ligands) and 5.96 (s, 2H=2×C$\underline{H}$ of thd ligands) . FIGS. 5b–5c further evidence the cis- to trans-equilibration of the sample over time as the peaks at 1.24 (s, 36H=4×—C(C$\underline{H}_3$)$_3$ of thd ligands) and 5.96 (s, 2H=2×C$\underline{H}$ of thd ligands) increase over the nine day period (FIG. 5b time lapse=24 hours, FIG. 5c time lapse=9 days). Such ). Such isomerization is accompanied by a disproportionation/dimerization reaction, leading to a less volatile, less soluble dinuclear species of Hf, making it less desirable for CVD applications.

NMR Characterization of $Zr(thd)_2(O-tBu)_2$

Figure 6A:
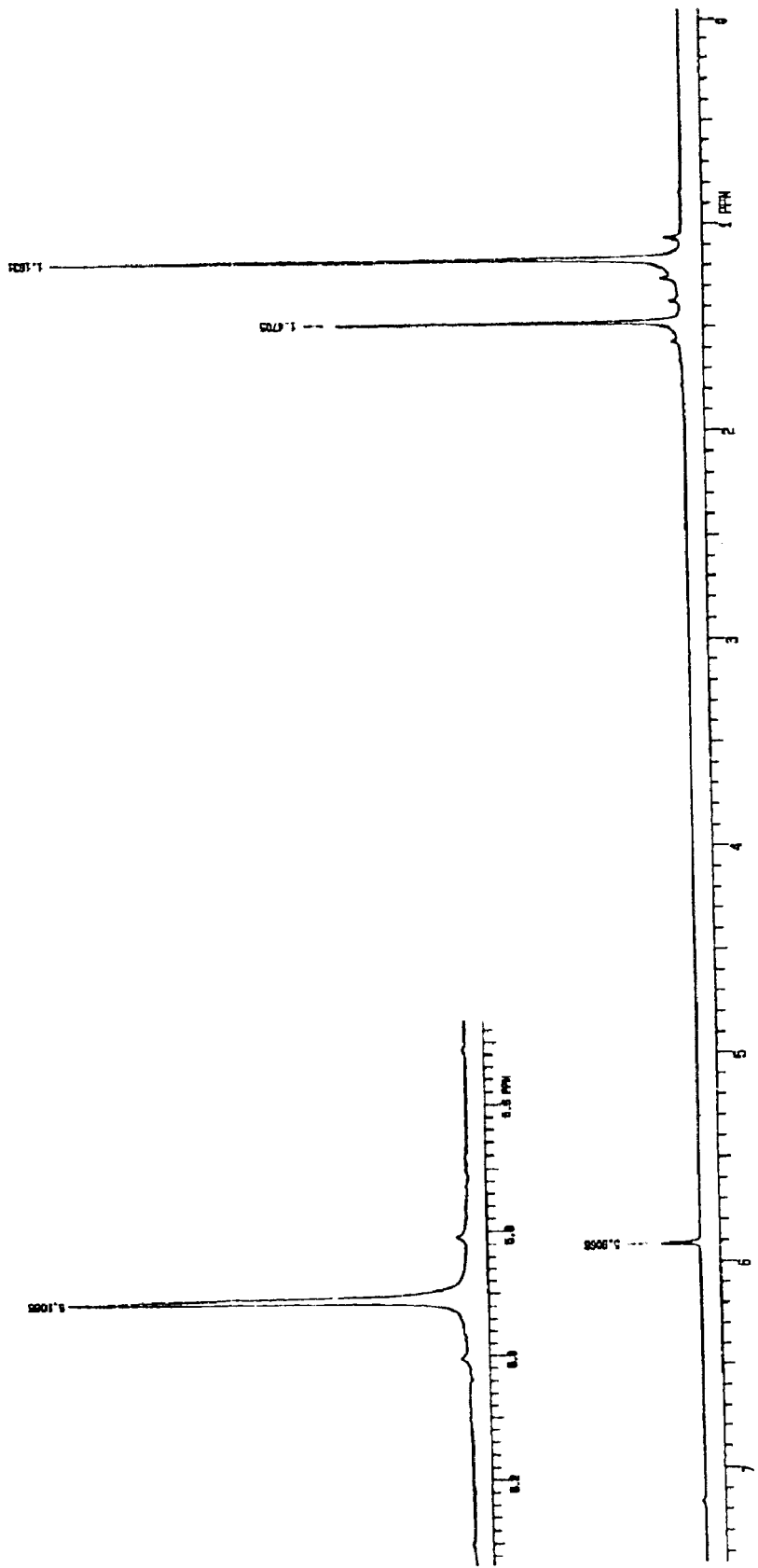
FIGS. 6a–6d are nuclear magnetic resonance (NMR) spectra of $Zr(thd)_2(O-tBu)_2$ in $C_6D_6$ showing no cis- and trans- isomers equilibration over time.
Figure 6B:
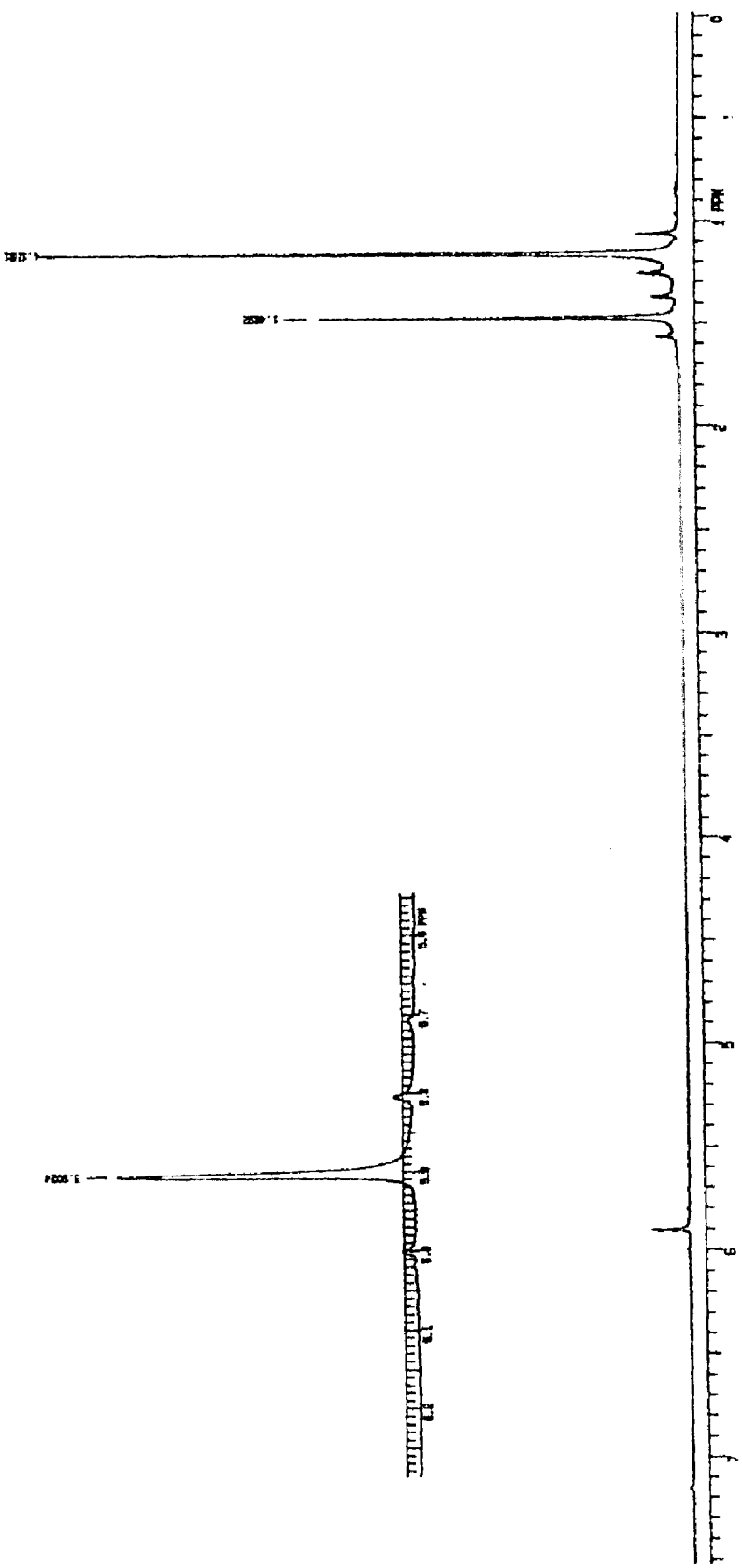
Figure 6C:
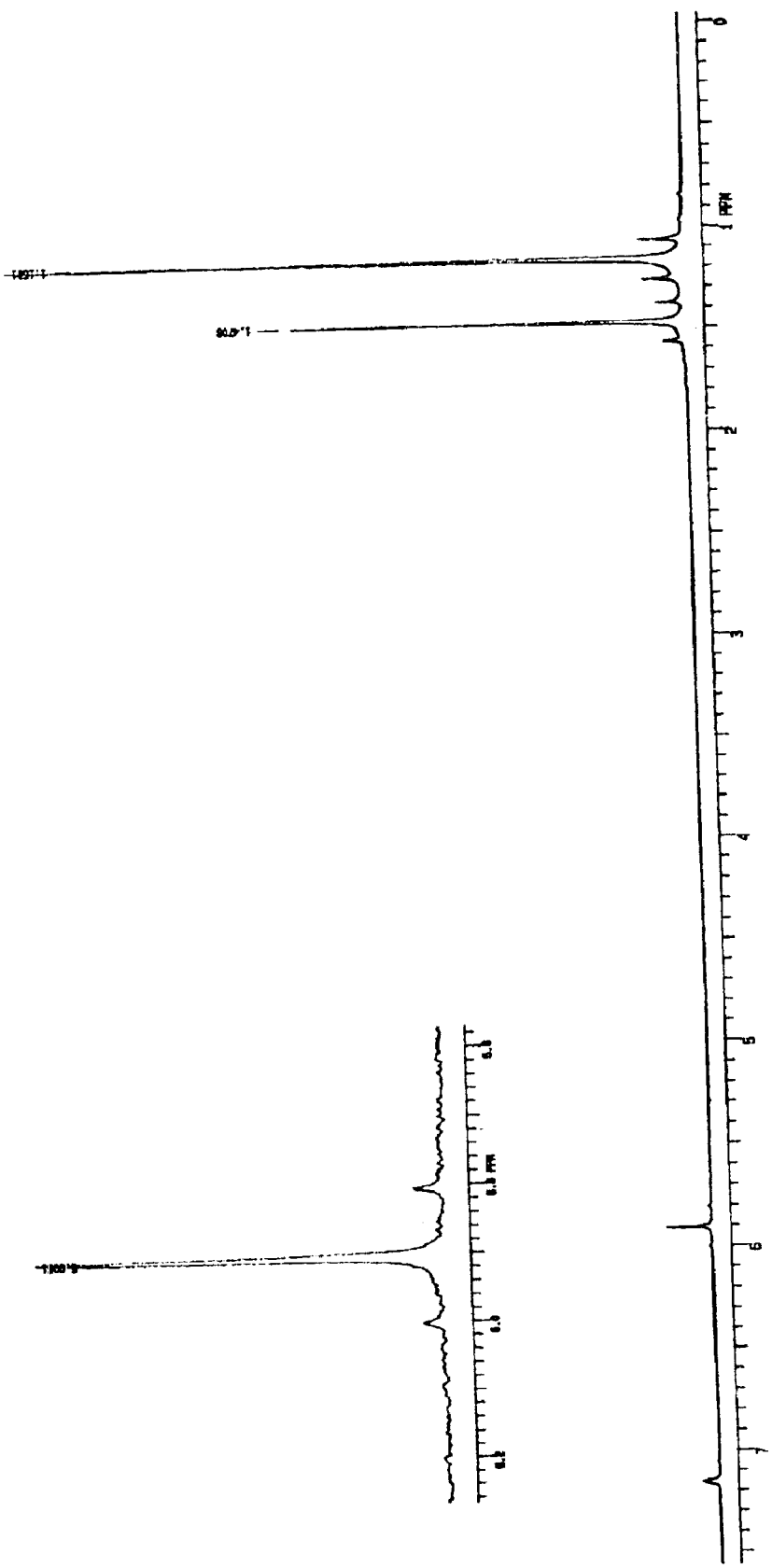
Figure 6D:
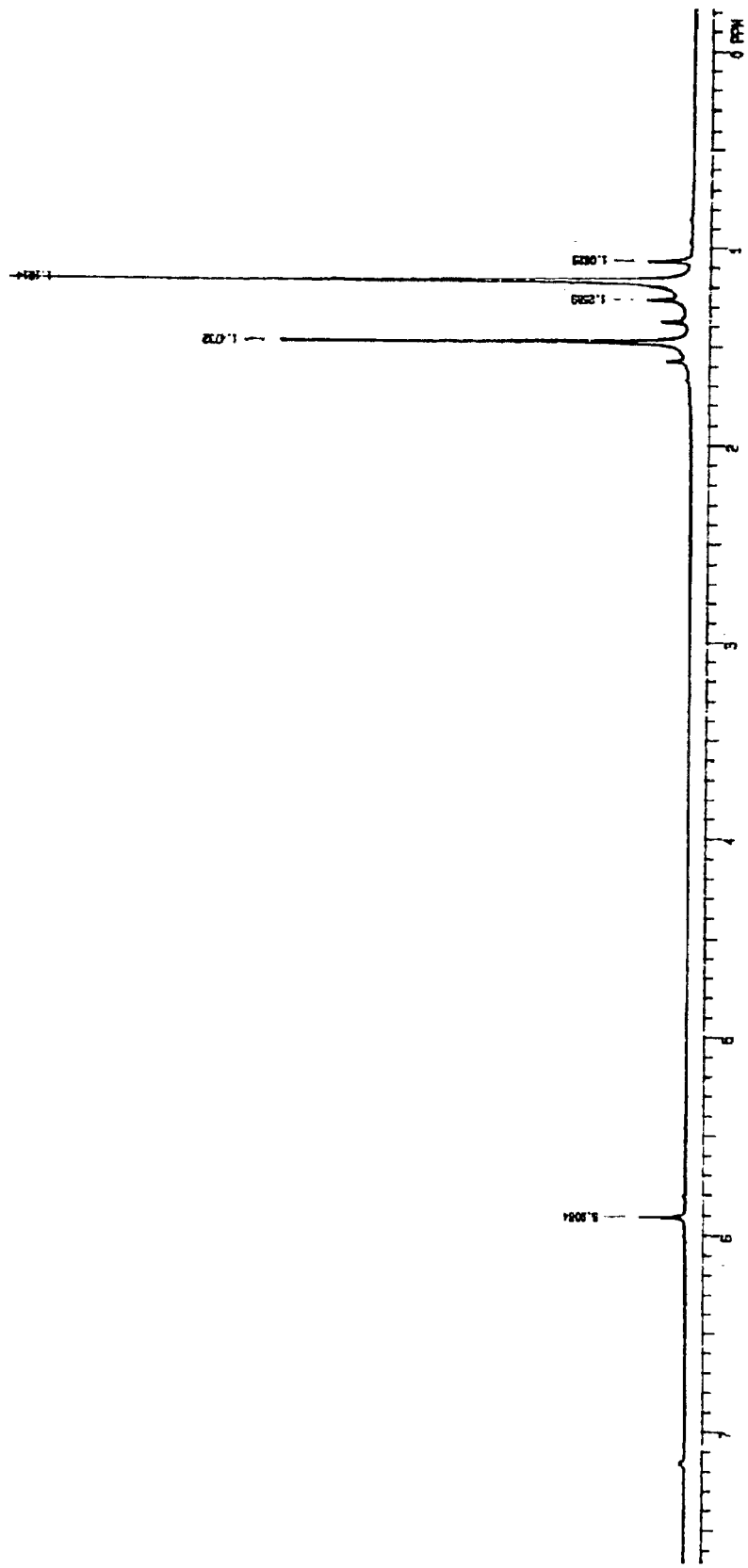

A sample of $Zr(thd)_2(O-tBu)_2$ is dissolved in deuterated benzene solvent. FIGS. 6a–6d, show the $^1H$ NMR ($C_6D_6$), δ (ppm) spectra of a single sample of $Zr(thd)_2(O-tBu)_2$ over a period of approximately twenty-nine days. The original sample in FIG. 6a shows essentially all of the compound to be in the cis-phase 1.16 (s, 36H=4×—C(C$\underline{H}_3$)$_3$ of thd ligands) and 5.91 (s, 2H=2×C$\underline{H}$ of thd ligands). FIGS. 6b–6d support the finding that the presence of the bulky t-butyl groups in the alkoxide ligands limit the occurrence of cis- to trans-equilibration and eliminates the proportionation or dimerization to dinuclear species over time, particularly when the compound is in an organic solution or suspension (FIG. 6b time lapse=3 days, FIG. 6c time lapse=13 days, FIG. 6d time lapse=29 days).

Synthesis and Characterization of $Zr(thd)_2(O-tBu)_2$

The synthesis of $Zr(thd)_2(O-tBu)_2$ was carried out under a steady flow of $N_2$. A 250 mL Schlenk flask was charged with 10.0 g (~0.0261 moles) of freshly distilled $Zr(O-tBu)_4$ in 100 mL of dry toluene or pentane solvent. The temperature of the solvent, whether pentane or toluene, was held at a temperature between about 0° C. to 5° C.

Approximately two equivalents of Hthd in the amount of 9.55 g (~0.0582 moles) were slowly added into the $Zr(O-tBu)_4$ solution under constant stirring by a magnetic stirring bar.

After complete addition of Hthd into the $Zr(O-tBu)_4$ solution, the mixture was stirred for several hours. The solvent was then removed from the mixture under vacuum.

A white solid product was isolated, constituting $Zr(thd)_2(O-tBu)_2$ in an amount of 15.7 g (~0.0261 moles), as a near quantitative yield of solid $Zr(thd)_2(O-tBu)_2$.

The yielded white solid was analyzed using NMR technique, wherein M.P.: 200° C.; $^1H$ NMR ($C_6D_6$), δ (ppm), 5.90 (s, 2H=2×C$\underline{H}$ of thd ligands), 1.47 (s, 18H=2×—OC(C$\underline{H}_3$)$_3$ of tert-butoxide), 1.16 (s, 36H=4×—C(C$\underline{H}_3$)$_3$ of thd ligands). See FIGS. 10 and 11. The protons of the t-butyl groups are magnetically equivalent at room temperature, indicating the presence of only cis-conformation within this molecule. In contrast, the $Zr(thd)_2(O-iPr)_2$ species displays the ability to form trans-conformer over time in solution. Therefore, the sterically bulky t-butyl groups limit the ability of the $Zr(thd)_2(O-tBu)_2$ molecule to undergo cis- to trans-equilibration and later proportionation to the dinuclear species $[Zr(thd)_2(O-tBu)_2]_2$.

Further, the $Zr(thd)_2(O-tBu)_2$ compound can be synthesized in higher elemental purity, relative to $Zr(thd)_2(O-iPr)_2$, as a result of the facile purification of $Zr(O-tBu)_4$ by distillation.

Deposition of $Pb(Zr,Ti)O_3$ Using $Zr(thd)_2(O-tBu)_2$ Compound Precursor

A solution of 0.15M $Pb(thd)_2$-pmdeta, 0.045M $Zr(thd)_2(O-tBu)_2$, and 0.105M $Ti(thd)_2(O-tBu)_2$ is prepared in an anhydrous solvent mixture containing 9 parts octane to 1 part pmdeta. This solution is metered to a vaporizer with temperatures controlled to 190° C. at a rate of 0.45 ml/min with 200 sccm of helium flow as a carrier gas. The precursor vapor is transported in temperature-controlled manifolds at 190° C. to a temperature-controlled showerhead at 190° C. in which the vapor is mixed with 500 sccm $O_2$ and 500 sccm $N_2O$ oxidizing gases. At the outlet of the showerhead, the gaseous mixture is contacted with a substrate with an iridium surface, which is heated to 580° C. The pressure in the chamber is maintained at 1 Torr by controlling the conductance of the chamber outlet to the vacuum pump.

The resulting film is approximately 51 at % (metals content) Pb and the Zr:Ti ratio is approximately 30:70. For a 10 minute deposition time, the film thickness is 150 nm, for an average growth rate of 15 nm/min.

Deposition of Amorphous Bi—Hf—O using $Hf(thd)_2(O-tBu)_2$ Compound Precursor

A solution of 0.10M $Bi(thd)_3$-pmdeta and 0.10M $Hf(thd)_2(O-tBu)_2$ is prepared in an anhydrous solvent mixture containing 9 parts octane to 1 part pmdeta. This solution is metered to a vaporizer with temperatures controlled to 190° C. at a rate of 0.30 ml/min with 200 sccm of helium flow as a carrier gas. The precursor vapor is transported in temperature-controlled manifolds at 190° C. to a temperature-controlled showerhead at 190° C. in which the vapor is mixed with 800 sccm $O_2$ oxidizing gas. At the outlet of the showerhead, the gaseous mixture is contacted with a substrate with a conducting surface (to be used as the capacitor bottom electrode), which is heated to 350° C. The pressure in the chamber is maintained at 10 Torr by controlling the conductance of the chamber outlet to the vacuum pump.

The resulting film is approximately 50 at % (metals content) Bi. For a 2 minute deposition time, the film thickness is 8 nm, for an average growth rate of 4 nm/min.

Deposition of $(Ba,Sr)(Zr,Ti)O_3$ Using $Zr(thd)_2(O-tBu)_2$ Compound Precursor

A solution of 0.125M $Ba(thd)_2$-pmdeta, 0.125M $Sr(thd)_2$-pmdeta, 0.20M $Ti(thd)_2(O-tBu)_2$ and 0.05M $Zr(thd)_2(O-tBu)_2$ is prepared in an anhydrous solvent mixture containing 9 parts butyl acetate to 1 part pmdeta. This solution is metered to a vaporizer with temperatures controlled to 230° C. at a rate of 0.10 ml/min with 200 sccm of helium flow as a carrier gas. The precursor vapor is transported in temperature-controlled manifolds at 230° C. to a temperature-controlled showerhead at 230° C. in which the vapor is mixed with 400 sccm $O_2$ and 400 sccm $N_2O$ oxidizing gases. At the outlet of the showerhead, the gaseous mixture is contacted with a substrate with a conducting surface (to be used as the capacitor bottom electrode), which is heated to 600° C. The pressure in the chamber is maintained at 0.8 Torr by controlling the conductance of the chamber outlet to the vacuum pump.

The resulting film is approximately 23 at % (metals content) Ba, 23 at % (metals content) Sr, 11 at % (metals content) Zr, and 43 at % (metals content) Ti. For a 2 minute deposition time, the film thickness is 8 nm, for an average growth rate of 4 nm/min.

The present invention provides efficient high purity zirconium and/or hafnium precursors. The precursors of the invention enable zirconium- and/or hafnium-containing films to be readily formed, exhibiting good electrical properties and low current leakages.

Although the invention has been variously disclosed herein with reference to illustrative embodiments and features, it will be appreciated that the embodiments and features described hereinabove are not intended to limit the invention, and that other variations, modifications, and other embodiments will suggest themselves to those of ordinary skill in the art. The invention therefore is to be broadly construed, consistent with the claims hereafter set forth.

What is claimed is:

1. A CVD source reagent composition for forming a metal oxide thin film, said source reagent composition comprising a metal precursor of the formula:

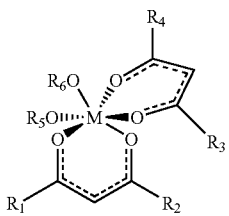

wherein:
M is Ti;
each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and
$R_5$ and $R_6$ are both t-butyl groups.

2. The CVD source reagent composition of claim 1, wherein the metal precursor comprises at least one β-diketonate moiety selected from the group consisting of 2,4-pentanedione (acac), 1,1,1-trifluoro-2,4-pentanedionato (tfac), 1,1,1,5,5,5-hexafluoro-2,4-pentanedionato (hfac), 2,2,6,6-tetramethyl-3,5-heptanedionato (thd), 2,2,7-trimethyl-3,5-octanedionato (tod), and 6,6,7,7,8,8-heptafluoro-2,2-dimethyl-3,5-octanedionato (fod).

3. The CVD source reagent composition of claim 1, further comprising a solvent medium.

4. The CVD source reagent composition of claim 3, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

5. The CVD source reagent composition of claim 3, wherein the solvent medium comprises octane.

6. The CVD source reagent composition of claim 3, wherein $Ti(thd)_2(O-tBu)_2$ has been synthesized by using a $Ti(O-tBu)_4$ solution comprising a solvent medium selected from the group consisting of aryl, hydrocarbon, and combinations thereof.

7. The CVD source reagent composition of claim 6, wherein the $Ti(O-tBu)_4$ solution comprises toluene.

8. The CVD source reagent composition of claim 6, wherein the $Ti(O-tBu)_4$ solution comprises pentane.

9. The CVD source reagent composition of claim 1, wherein the metal precursor comprises $Ti(thd)_2(O-tBu)_2$.

10. The CVD source reagent composition of claim 9, wherein said source reagent composition further comprises $Pb(thd)_2$pmdeta.

11. The CVD source reagent composition of claim 10, further comprising a solvent medium.

12. The CVD source reagent composition of claim 11, wherein the solvent medium comprises a mixture of octane and pmdeta.

13. The CVD source reagent composition of claim 12, wherein the solvent medium comprises a mixture of octane and pmdeta in a volumetric ratio of 9 parts octane to 1 part pmdeta.

14. The CVD source reagent composition of claim 9, wherein $Ti(thd)_2(O-tBu)_2$ has been synthesized by a synthetic procedure including the following reaction:

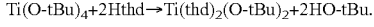

15. The CVD source reagent composition of claim 9, further comprising a solvent medium.

16. The CVD source reagent composition of claim 15, wherein the solvent medium comprises a mixture of octane and pmdeta.

17. The CVD source reagent composition of claim 15, wherein the solvent medium comprises a mixture of octane and pmdeta in a volumetric ratio of 9 parts octane to 1 part pmdeta.

18. The CVD source reagent composition of claim 9, further comprising $Zr(thd)_2(O-tBu)_2$.

19. The CVD source reagent composition of claim 18, further comprising $Pb(thd)_2$pmdeta.

20. The CVD source reagent composition of claim 19, further comprising a solvent medium.

21. The CVD source reagent composition of claim 1, further comprising $Zr(thd)_2(O-tBu)_2$.

22. The CVD source reagent composition of claim 21, wherein said source reagent composition further comprises $Pb(thd)_2$pmdeta.

23. The CVD source reagent composition of claim 15, further comprising a solvent medium.

24. The CVD source reagent composition of claim 23, wherein the solvent medium comprises butyl acetate and pmdeta.

25. The CVD source reagent of claim 24, wherein the solvent medium comprises butyl acetate and pmdeta in a volumetric ratio of 9 parts butyl acetate to 1 part pmdeta.

26. The CVD source reagent composition of claim 21, further comprising a solvent medium.

27. The CVD source reagent composition of claim 26, wherein the solvent medium comprises butyl acetate and pmdeta.

28. The CVD source reagent of claim 27, wherein the solvent medium comprises butyl acetate and pmdeta in a volumetric ratio of 9 parts butyl acetate to 1 part pmdeta.

29. The CVD source reagent composition of claim 1, further comprising $Hf(thd)_2(O\text{-}tBu)_2$.

30. The CVD source reagent composition of claim 29, further comprising a solvent medium.

31. The CVD source reagent composition of claim 30, wherein the solvent medium comprises butyl acetate and pmdeta.

32. The CVD source reagent of claim 31, wherein the solvent medium comprises butyl acetate and pmdeta in a volumetric ratio of 9 parts butyl acetate to 1 part pmdeta.

33. The CVD source reagent composition of claim 1, wherein the metal oxide thin film is selected from the group consisting of:

$PbTiO_3$ $PbZr_xTi_{1-x}O_3$, wherein x=0 to 1, $Ba_ySr_{1-y}Zr_xTi_{1-x}O_3$, wherein x=0 to 1 and y=0 to 1.

34. The CVD source reagent composition of claim 1 further comprising a metal precursor of the formula:

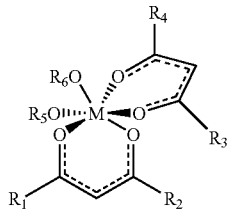

wherein:

M is selected from the group consisting of Zr and Hf;

each of $R_1$, $R_2$, $R_3$, and $R_4$ is independantly selected from the group consisting of H, aryl, perfluoroaryl, $C_1$–$C_8$ alkyl, and $C_1$–$C_8$ perfluoroalkyl; and $R_4$ and $R_5$ are both t-butyl groups.

35. The CVD source reagent composition of claim 34, further comprising a solvent medium.

36. The CVD source reagent composition of claim 1, further comprising $Pb(thd)_2$pmdeta.

37. The CVD source reagent composition of claim 36, further comprising a solvent medium.

38. A method of forming a metal oxide thin film, comprising the steps of:

vaporizing the CVD source reagent composition of claim 1 to form a source reagent vapor;

transporting said source reagent vapor into a chemical vapor deposition zone, optionally using a carrier gas; and contacting the source reagent vapor with a substrate in said chemical vapor deposition zone in the presence of an oxidizer and at elevated temperature to deposit a high dielectric constant or ferroelectric metal oxide thin film on the substrate.

39. The method of claim 38, wherein the metal precursor in said CVD source reagent composition comprises at least one β-diketonate moiety selected from the group consisting of 2,4-pentanedione (acac),1,1,1-trifluoro-2,4-pentanedionato (tfac), 1,1,1,5,5,5-hexafluoro-2,4-pentanedionato (hfac), 2,2,6,6-tetramethyl-3,5-heptanedionato (thd), 2,2,7-trimethyl-3,5-octanedionato (tod), and 6,6,7,7,8,8-heptafluoro-2,2-dimethyl-3,5-octanedionato (fod).

40. The method of claim 38, wherein said CVD source reagent composition further comprises a solvent medium.

41. The method of claim 40, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

42. The method of claim 40, wherein the solvent medium comprises octane.

43. The method of claim 38, wherein the metal precursor in said CVD source reagent composition comprises $Ti(thd)_2(O\text{-}tBu)_2$.

44. The method of claim 43, wherein said CVD source reagent composition further comprises $Pb(thd)_2$pmdeta.

45. The method of claim 44, wherein said CVD source reagent composition further comprises a solvent medium.

46. The method of claim 45, wherein the solvent medium comprises butyl acetate and pmdeta.

47. The method of claim 46, wherein the solvent medium comprises butyl acetate and pmdeta in a volumetric ratio of 9 parts butyl acetate to 1 part pmdeta.

48. The method of claim 43, wherein $Ti(thd)_2(O\text{-}tBu)_2$ has been synthesized by a synthetic procedure including the following reaction:

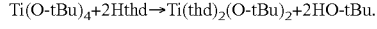

$Ti(O\text{-}tBu)_4 + 2Hthd \rightarrow Ti(thd)_2(O\text{-}tBu)_2 + 2HO\text{-}tBu.$ 49. The method of claim 43, wherein $Ti(thd)_2(O\text{-}tBu)_2$ has been synthesized by using a $Ti(O\text{-}tBu)_4$ solution comprising a solvent medium selected from the group consisting of aryl, hydrocarbon, and combinations thereof.

50. The method of claim 49, wherein the $Ti(thd)_2(O\text{-}tBu)_2$ solution comprises toluene.

51. The method of claim 49, wherein the $Ti(thd)_2(O\text{-}tBu)_2$ solution comprises pentane.

52. The method of claim 38, wherein the CVD source reagent composition further comprises $Zr(thd)_2(O\text{-}tBu)_2$.

53. The method of claim 38, wherein said CVD source reagent composition further comprises $Hf(thd)_2(O\text{-}tBu)_2$.

54. The method of claim 38, wherein the metal oxide thin film is selected from the group consisting of:

$PbTiO_3$ $PbZr_xTi_{1-x}O_3$, wherein x=0 to 1, $Ba_ySr_{1-y}Zr_xTi_{1-x}O_3$, wherein x=0 to 1 and y=0 to 1.

55. The method of claim 38, wherein the step of vaporizing the source reagent composition is carried out at a vaporization temperature in a range of from about 100° C. to about 300° C.

56. The method of claim 38, wherein a carrier gas is used for transporting the source reagent vapor and said carrier gas comprises argon.

57. The method of claim 38, wherein a carrier gas is used for transporting the source reagent vapor and said carrier gas comprises helium.

58. The method of claim 38, wherein the oxidizer comprises oxygen.

59. The method of claim 38, wherein the metal oxide thin film is deposited on the substrate at a deposition temperature in a range of from about 300° to about 750° C.

60. A method for forming the CVD source reagent composition of claim 1, comprising forming $Ti(thd)_2(O\text{-}tBu)_2$ by a synthetic procedure that includes the following reaction:

$$Ti(O\text{-}tBu)_4 + 2Hthd \rightarrow Ti(thd)_2(O\text{-}tBu)_2 + 2HO\text{-}tBu$$

and, combining the metal precursor formed with a medium in which it is soluble or suspendable.

61. A method for forming the CVD source reagent composition of claim 1, comprising forming $Ti(thd)_2(O\text{-}tBu)_2$ using a $Ti(O\text{-}tBu)_4$ solution that comprises a solvent medium selected from the group consisting of aryl, hydrocarbon, and combinations thereof.

62. The method of claim 61, wherein the $Ti(thd)_2(O\text{-}tBu)_2$ solution comprises toluene.

63. The method of claim 61, wherein the $Ti(thd)_2(O\text{-}tBu)_2$ solution comprises pentane.

* * * * *